United States Patent

Neurath

US 6,462,030 B1
Oct. 8, 2002

(54) METHOD FOR INACTIVATING BACTERIA ASSOCIATED WITH BACTERIAL VAGINOSIS USING CELLULOSE ACETATE PHTHALATE AND/OR HYDROXYPROPYL METHYCELLULOSE PHTHALATE

(75) Inventor: Alexander R. Neurath, New York, NY (US)

(73) Assignee: New York Blood Center, Inc., New York, NY (US)

(*) Notice: Subject to any disclaimer, the term of this patent is extended or adjusted under 35 U.S.C. 154(b) by 29 days.

(21) Appl. No.: 09/596,623

(22) Filed: Jun. 19, 2000

Related U.S. Application Data

(60) Provisional application No. 60/144,454, filed on Jul. 19, 1999.

(51) Int. Cl.[7] .................................. A61K 31/717
(52) U.S. Cl. ........................................ 514/57
(58) Field of Search .................................. 514/57

(56) References Cited

U.S. PATENT DOCUMENTS 5,314,904 A * 5/1994 Edigio et al. ............... 514/394
5,741,525 A    4/1998 Larsen
5,985,313 A   11/1999 Neurath et al. ............ 424/430
6,165,493 A * 12/2000 Neurath ..................... 424/432

OTHER PUBLICATIONS

Sewankambo, N., Gray R.H., Wawer et al., M.J., "HIV–1 Infection Associated with Abnormal Vaginal Flora Morphology and Bacterial Vaginosis", *Lancet*, 350, 546–550, (1997).
Taha, T.E., Hoover, D.R., Dallabeta et al., G.A., "Bacterial Vaginosis and Disturbances of Vaginal Flora: Association with Increased Acquisition of HIV", *AIDS*, 12, 1699–1706, (1998).
Cohen, C.R., Duerr, A., Pruithithada et al., N., "Bacterial Vaginosis and HIV Seroprevalence Among Female Commercial Sex Workers in Chiang Mai, Thailand", *AIDS*, 9, 1093–1097, (1995).
Sobel, J.D., "Vaginitis", *New England J. Med.*, 337, 1896–1903, (1997).

Carr, P.L., Felsenstein, D., Friedman, R.H., "Evaluation and Management of Vaginitis", *J. Gen. Intern. Med.*, 13, 335–346, (1998).
Schwebke, J.R., "Bacterial Vaginosis—More Questions Than Answers" [editorial], *Genitourin Med.*, 73, 333–334, (1997).
Lee, J.C., (1994), "Cellulose acetate phthalate", *Handbook of Pharmaceutical Excipients*, 2nd Ed., Wade, A. and Weller, P.J., pp. 91–93, American Pharmaceutical Association Publishers, Washington, D.C.
Neurath, A.R., Strick, N., Li, Y–Y, Jiang, S., "Design of a 'Microbicide' for Prevention of Sexually Transmitted Diseases Using 'Inactive' Pharmaceutical Excipients", *Biologicals*, 27, 11–21, (1999).
Martin, Jr., H.L., Richardson, B.A., Nyange, P., Lavreys, L., Hiller, S.L., Chohan, B. et al. (1999), "Vaginal Lactobacilli, Microbial Flora, and Risk of Human Immunodeficiency Virus Type 1 and Sexually Transmitted Disease Acquisition", *Journal of Infectious Diseases*, 180, 1863–1868.
Klebanoff, S.J., Coombs, R.W., "Viricidal Effect of Lactobacillus Acidophilus on Human Immunodeficiency Virus Type 1: Possible Role in Heterosexual Transmission", *J. Exp. Med.*, 174, 289–292, (1991).
Gyotoku, T., Aurelian, L. and Neurath, A.R., "Cellulose Acetate Phthalate (CAP) : An 'Inactive' Pharmaceutical Excipient with Antiviral Activity in the Mouse Model of Genital Herpesvirus Infection", *Antiviral Chemistry & Chemotherapy*, 10, 327–332, (1999).
Hill, G.B., "The Microbiology of Bacterial Vaginosis", *Am. J. Obstet. Gynecol.*, 169, 450–454, (1993).

* cited by examiner

Primary Examiner—James O. Wilson
Assistant Examiner—Leigh C. Maier
(74) Attorney, Agent, or Firm—Frishauf, Holtz, Goodman & Chick, P.C.

(57) ABSTRACT

A method for treating or preventing bacterial vaginosis comprising administering to a human female an effective anti-bacterial vaginosis amount of a composition comprising at least one active compound selected from the group consisting of cellulose acetate phthalate and hydroxypropyl methylcellulose phthalate, either alone or in combination with a pharmaceutically acceptable carrier.

18 Claims, 3 Drawing Sheets

METHOD FOR INACTIVATING BACTERIA ASSOCIATED WITH BACTERIAL VAGINOSIS USING CELLULOSE ACETATE PHTHALATE AND/OR HYDROXYPROPYL METHYCELLULOSE PHTHALATE

CROSS-REFERENCE TO RELATED APPLICATION

The present application claims the benefit of Provisional Application Ser. No. 60/144,454, filed Jul. 19, 1999, wherein priority under 35 USC 119(e) is claimed.

BACKGROUND OF THE INVENTION

1. Field of the Invention

The present invention concerns a method for treating or preventing bacterial vaginosis using cellulose acetate phthalate and/or hydroxypropyl methylcellulose phthalate.

2. Background Information

Recent findings suggest that bacterial vaginosis ("BV") may increase susceptibility to HIV-1 infection (Sewankambo, EN., Gray R. H., Wawer et al., M. J., "HIV-1 Infection Associated with Abnormal Vaginal Flora Morphology and Bacterial Vaginosis", *Lancet*, 350, 546–550, (1997); Taha, T. E., Hoover, D. R., Dallabeta et al., G. A., "Bacterial Vaginosis and Disturbances of Vaginal Flora: Association with Increased Acquisition of HIV", *AIDS*, 12, 1699–1706, (1998); Cohen, C. R., Duerr, A., Pruithithada et al., N., "Bacterial Vaginosis and HIV Seroprevalence Among Female Commercial Sex Workers in Chiang Mai, Thailand", *AIDS*, 9, 1093–1097, (1995)). Depending on the population studied, up to nearly 40% of selected groups may have BV (Sobel, J. D., "Vaginitis", *New England J. Med.*, 337, 1896–1903, (1997)). Although unequivocal evidence that BV is a sexually transmitted disease is lacking (Carr, P. L., Felsenstein, D., Friedman, R. H., "Evaluation and Management of Vaginitis", *J. Gen. Intern. Med.*, 13, 335–346, (1998)), BV behaves in many ways as if it were a sexually transmitted disease ("STD") (Schwebke, J. R., "Bacterial Vaginosis—More Questions Than Answers" [editorial], *Genitourin Med.*, 73, 333–334, (1997)). Therefore, treatment of BV is expected to contribute to controlling the spread of STDs, including HIV-1 (Schwebke, J. R., "Bacterial Vaginosis—More Questions Than Answers" [editorial], *Genitourin Med.*, 73, 333–334, (1997)).

It has recently been reported that cellulose acetate phthalate ("CAP") (Eastman Kingston, Tenn., USA) which has heretofore been used as an excipient for the enteric coating of tablets and capsules (Lee, J. C., (1994), Cellulose acetate phthalate, *Handbook of Pharmaceutical Excipients*, 2nd Ed., Wade, A. and Weller, P. J., pp. 91–93, American Pharmaceutical Association Publishers, Washington, D.C.), has antiviral activity in vitro against HIV-1 and herpesviruses ("HSV") and, when appropriately formulated, inactivated HIV-1, herpesviruses and several bacterial STD pathogens without affecting Lactobacilli (Neurath, A. R., Strick, N., Li, Y-Y, Jiang, S., "Design of a 'Microbicide' for Prevention of Sexually Transmitted Diseases Using 'Inactive' Pharmaceutical Excipients", *Biologicals*, 27, 11–21, (1999)), essential for maintaining a normal vaginal flora (Martin, Jr., H. L., Richardson, B. A., Nyange, P., Lavreys, L., Hiller, S. L., Chohan, B. et al. (1999), "Vaginal Lactobacilli, Microbial Flora, and Risk of Human Immunodeficiency Virus Type 1 and Sexually Transmitted Disease Acquisition", *Journal of Infectious Diseases*, 180, 1863–1868), (*Handbook of Pharmaceutical Excipients*), Wade, A. and Weller, P. J., eds., 2nd Ed., American Pharmaceutical Association, (1994); Klebanoff, S. J., Coombs, R. W., "Viricidal Effect of Lactobacillus Acidophilus on Human Immunodeficiency Virus Type 1: Possible Role in Heterosexual Transmission", *J. Exp. Med.*, 174, 289–292, (1991)). These findings have been further strengthened by the favorable outcome of experiments in the HSV-2/mouse (Gyotoku, T., Aurelian, L. and Neurath, A. R., "Cellulose Acetate Phthalate (CAP): An 'Inactive' Pharmaceutical Excipient with Antiviral Activity in the Mouse Model of Genital Herpesvirus Infection", *Antiviral Chemistry & Chemotherapy*, 10, 327–332, (1999)) and simian immunodeficiency virus/monkey models for vaginal infection.

Considering the role of BV in susceptibility to infection by HIV-1 and other STD pathogens, it seemed important to the present inventor to also evaluate the effect of CAP on microorganisms associated with BV, namely, *Gardnerella Vaginalis*, Mycoplasmas, *Mobiluncus curtisii* and *Prevotella corporis* (Sobel, J. D., "Vaginitis", *New England J. Med.*, 337, 1896–1903, (1997); Schwebke, J. R., "Bacterial Vaginosis—More Questions Than Answers" [editorial], *Genitourin Med.*, 73, 333–334, (1997); Hill, G. B., "The Microbiology of Bacterial Vaginosis", *Am. J. Obstet. Gynecol.*, 169, 450–454, (1993)).

Heretofore uses of CAP are described in U.S. Pat. No. 5,985,313 and U.S. application Ser. No. 09/175,909.

SUMMARY OF THE INVENTION

It is an object of the present invention to provide a method for treating and preventing bacterial vaginosis.

The present invention concerns a method for treating or preventing bacterial vaginosis comprising administering to a human female an effective anti-bacterial vaginosis amount of a composition comprising at least one active compound selected from the group consisting of cellulose acetate phthalate and hydroxypropyl methylcellulose phthalate, either alone or in combination with a pharmaceutically acceptable carrier.

BRIEF DESCRIPTION OF THE DRAWINGS

FIG. 1A shows selected images of agar plates plated with dilutions of bacteria treated with CAP containing and control formulations. FIG. 1B is a graph showing the relationship between the number of bacterial colonies and dilutions of bacterial suspensions exposed to formulations containing CAP and control formulations or to PBS.

DETAILED DESCRIPTION OF THE INVENTION

Figure 1A:
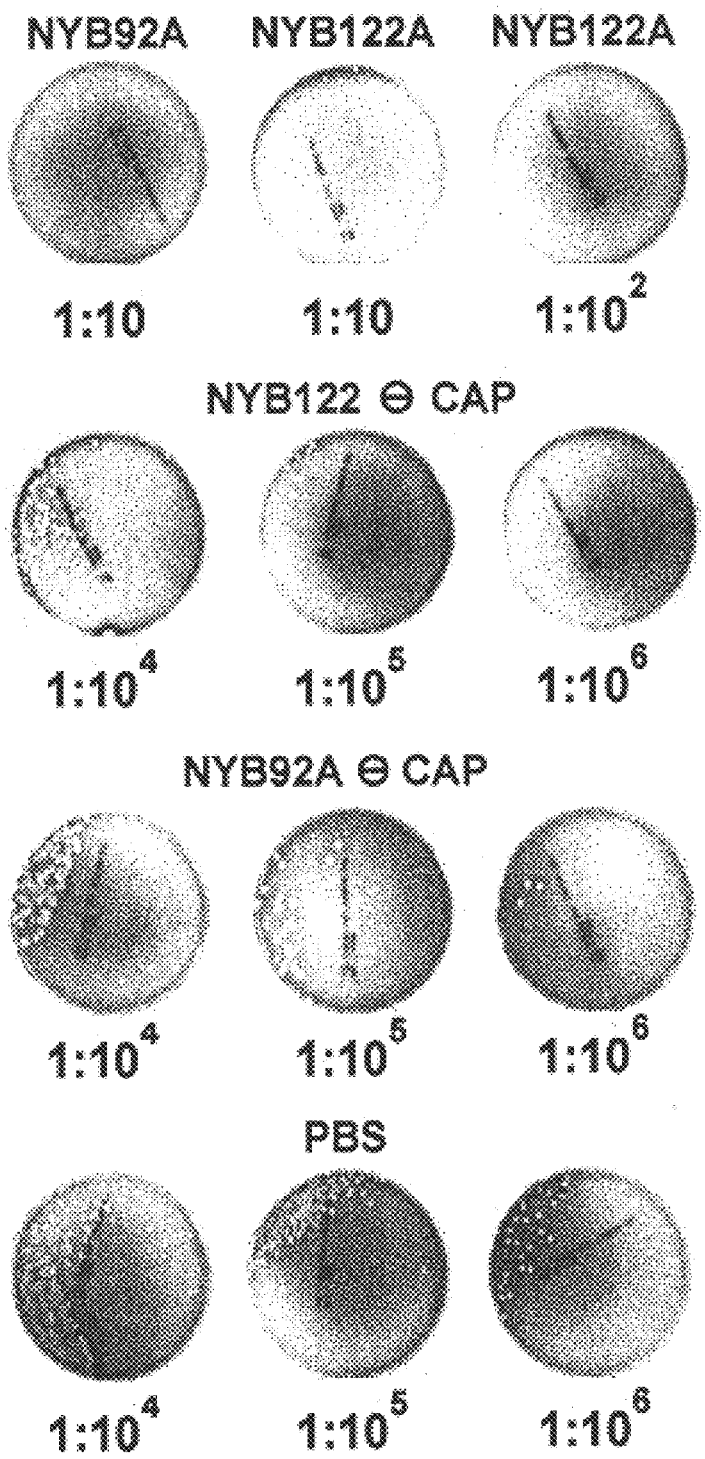
FIGS. 1A and 1B show the effect of CAP and control formulations on *Gardnerella vaginalis* (co-incubation for 15 minutes at 37° C.).

The present invention concerns the administration of at least one compound selected from the group consisting of cellulose acetate phthalate and hydroxypropyl methylcellulose phthalate.

In an embodiment of the present invention, micronized cellulose acetate phthalate (CAP) formulated into a cream is utilized for topical vaginal application to inactivate selected bacteria associated with bacterial vaginosis.

Without wishing to be bound by any particular theory of operability, the phthalic acid residues of CAP appear essential for antiviral and microbicidal activity, probably by providing a low PH buffering system and hydrophobicity, mimicking the effect of detergents, while remaining in a micronized form in the vaginal environment.

The fastest way to introduce topical microbicides into practice would be the application of already approved (for other uses) drugs or pharmaceutical ingredients. Such microbicides should: a) preferably not be spread systemically after topical application; b) be inexpensive; c) be produced from widely available resources; d) have a broad specificity, resulting in the prevention of transmission of several STDs; e) have a well-established, documented safety record; and f) inactivate the infectivity of the respective STD pathogens, as implied in the word "microbicide".

In order to meet the criteria for preferred microbicides, commonly used and already approved pharmaceutical excipients were first screened for anti-HIV activity. The screening revealed that one of the excipients CAP, had good anti-HIV-1 activity in vitro (Neurath, A. R., Strick, N., Li, Y-Y, Lin, K., Jiang, S., "Design of a 'microbicide' for Prevention of Sexually Transmitted Diseases using 'Inactive' Pharmaceutical Excipients", Biologicals, 27, 11–21, (1999)). CAP also inhibited infection by several herpesviruses. The compound formulated into a cream suitable for topical application inactivated after short exposure, HIV, several herpesviruses and the bacterial pathogens *Trichomonas vaginalis, Neisseria gonorrhea, Haemophilus ducreyi,* and *Chlamydia trachomatis* (Neurath, A. R., Strick, N., Li, Y-Y, Lin, K., Jiang, S., "Design of a 'microbicide' for Prevention of Sexually Transmitted Diseases using 'Inactive' Pharmaceutical Excipients", Biologicals, 27, 11–21, (1999)). The cream had no effect on Lactobacilli, a natural component of the vaginal flora contributing to resistance against transmission of several STDs. In vivo experiments in animal models revealed that the CAP cream had no irritating effects on vaginal tissues; had a pronounced antiviral activity in the mouse model (Gyotoku, T., Aurelian, L. and Neurath, A. R., "Cellulose Acetate Phthalate (CAP): An 'Inactive' Pharmaceutical Excipient With Antiviral Activity in the Mouse Model of Genital Herpesvirus Infection", Antiviral Chemistry & Chemotherapy, 10, pp. 327–332, (1999)) for genital herpesvirus infection and in the monkey model for genital simian immunodeficiency virus infection.

Cellulose acetate phthalate is characterized as follows.

USPNF: Cellulose acetate phthalate

Synonyms:

Acetyl phthalyl cellulose; CAP; cellacefate; cellulose acetate hydrogen 1,2-benzenedicarboxylate; cellulose acetate hydrogen phthalate; cellulose acetate monophthalate; cellulose acetophthalate; cellulose acetylphthalate.

Chemical Name and CAS Registry Number:

Cellulose, acetate, 1,2-benzenedicarboxylate [9004-38-0] Cellulose acetate phthalate is a cellulose in which about half the hydroxyl groups are acetylated and about a quarter are esterified, with one of the two acid groups being phthalic acid. The other acid group is free. See the structural formula below.

Structural Formula:

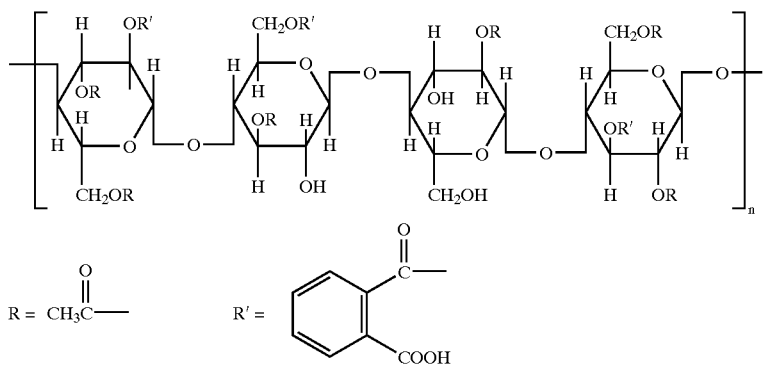

Functional Category:

Coating agent.

Applications in Pharmaceutical Formulation or Technology:

Cellulose acetate phthalate has heretofore been used as an enteric film coating material, or as a matrix binder, for tablets and capsules (Spitael, J., Kinget, R., Naessens, K., "Dissolution Rate of Cellulose Acetate Phthalate and Bronsted Catalysis Law", Pharm. Ind., (1980), 42:846–849; Tanenaka, H., Kawashima, Y., Lin, S. Y., "Preparation of Enteric-Coated Microcapsules for Tableting by Spray-Drying Technique and in vitro Stimulation of Drug Release from the Tablet in GI Tract", J. Pharm. Sci., (1980), 69:1388–1392; Stricker, H., Kulke, H., "Rate of Disintegration and Passage of Enteric-Coated Tablets in Gastrointestinal Tract", Pharm. Ind., (1981), 43:1018–1021; Tanenaka, H., Kawashima, Y., Lin, S-Y, "Polymorphism of Spray-Dried Microencapsulated Sulfamethoxazole with Cellulose Acetate Phthalate and Colloidal Silica Montomorillonite, or Talc", J. Pharm. Sci., (1981), 70:1256–1260; Maharaj, I., Nairn, J. G., Campbell, J. B., "Simple Rapid Method For the Preparation of Enteric-Coated Microspheres", J. Pharm. Sci., (1984), 73:39–42; Beyger, J. W., Nairn, J. G., "Some Factors Affecting the Microencapsulation of Pharmaceuticals with Cellulose Acetate Phthalate", J. Pharm. Sci., (1986), 75:573–573; Lin, S-Y, Kawashima, Y., "Drug Release from Tablets Containing Cellulose Acetate Phthalate as an Additive or Enteric-Coating Material", Pharm. Res., (1987), 4:70–74; Thoma, K. Hekenmuller, H., "Effect of Film Formers and Plasticizers on Stability of Resistance and Disintegration Behaviour, Part 4: Pharmaceutical-Technological and Analytical Studies of Gastric Juice Resistant Commercial Preparations", Pharmazie, (1987), 42:837–341).

Such coatings resist prolonged contact with the strongly acidic gastric fluid, but soften and swell in the mildly acidic or neutral intestinal environment.

Cellulose acetate phthalate, when heretofore used as an adjuvant, was commonly applied to solid dosage forms either by coating from organic or aqueous solvent systems, or by direct compression. Concentrations used were 0.5 to 9.0% of the core weight. The addition of plasticizers improves the water resistance of this coating material, and such plasticized films are more effective than when cellulose acetate phthalate is used alone as an adjuvant. Cellulose acetate phthalate is compatible with the following plasticizers: acetylated monoglyceride; butyl phthalylbutyl glycolate; dibutyl tartrate; diethyl phthalate; dimethyl phthalate; ethyl phthalyethyl glycolate; glycerin; propylene glycol; triacetin; triacetin citrate and tripropionin. Cellulose acetate phthalate has also been used heretofore in combination with other coating agents to control drug release, e.g., ethylcellulose.

Description:

Cellulose acetate phthalate is a hygroscopic, white, free-flowing powder or is in the form of colorless flakes. It is tasteless and odorless, or may have a slight odor of acetic acid.

Pharmacopeial Specifications:

| Test | PhEur 1984 | USPNF XVII (Suppl 2) |
|---|---|---|
| Identification | + | + |
| Appearance of solution | + | − |
| Appearance of a film | + | − |
| Solubility of a film | + | − |
| Viscosity at 25° C. | − | 45–90 cP |
| Water | ≦5.0% | ≦5.0% |
| Residue on ignition | − | ≦0.1% |
| Sulfated ash | ≦0.1% | − |
| Free acid | ≦3.0% | ≦6.0% |
| Heavy metals | ≦10 ppm | − |
| Phthalyl content | 30.0–40.0% | 30.0–36.0% |
| Acetyl content | 17.0–26.0% | 21.5–26.0% |

Typical Properties:

Hygroscopicity: cellulose acetate phthalate is hygroscopic and precautions are necessary to avoid excessive absorption of moisture (Callahan, J. C., Cleary, G. W., Elefant, M., Kaplan, G., Kensler, T., Nash, R. A., "Equilibrium Moisture Content of Pharmaceutical Excipients", *Drug Dev. Ind. Pharm.*, (1982), 8:355-369). Melting point: 192° C. Glass transition temperature is 160–170° C. (Sakellariou, P., Rowe, R. C., White, E. F. T., "The Thermomechanical Properties and Glass Transition Temperatures of Some Cellulose Derivatives used in Film Coating", *Int. J. Pharmaceutics*, (1985), 27:267–277). Solubility: practically insoluble in alcohols, chlorinated hydrocarbons, hydrocarbons, and water; soluble in cyclic ethers, esters, ether alcohols, ketones and certain solvent mixtures. Also soluble in certain buffered aqueous solutions at greater than pH 6. The following list shows some of the solvents and solvent mixtures in which cellulose acetate g phthalate has a solubility of 1 in 10 parts or more.

Acetone
Acetone: Ethanol (1:1)
Acetone: Methanol (1:1/1:3)
Acetone: Methylene chloride (1:1/1:3)
Acetone: Water (97.3)
Benzene: Methanol (1:1)
Diacetone alcohol
Dioxane
Ethoxyethyl acetate
Ethyl acetate: Ethanol (1:1)
Ethyl acetate: Propan-2-ol (1:1/1:3)
Ethylene glycol monoacetate
Ethyl lactate
Methoxyethyl acetate
β-Methoxyethylene alcohol
Methyl acetate
Methylene chloride: Ethanol (3:1)
Methyl ethyl ketone Viscosity (dynamic): 50–90 mPas (50–90 cp) for a 15% w/w solution in acetone with a moisture content of 0.4%. This is a good coating solution with a honey-like consistency, but the viscosity is influenced by the purity of the solvent.

Stability and Storage Conditions:

Cellulose acetate phthalate hydrolyzes slowly under prolonged adverse conditions, such as high temperature and humidity, with a resultant increase in free acid content, viscosity and odor of acetic acid. If its moisture content is above about 6% w/w, fairly rapid hydrolysis occurs. However, cellulose acetate phthalate is stable if stored in a well-closed container in a cool, dry place.

Incompatibilities:

Cellulose acetate phthalate is incompatible with ferrous sulfate, ferric chloride, silver nitrate, sodium citrate, aluminum sulfate calcium chloride, mercuric chloride, barium nitrate, basic lead acetate, and strong oxidizing agents such as strong alkalis and acids. It should be noted that one carboxylic acid group of the phthalic acid moiety remains unesterified and free for interactions. Accordingly, incompatibility with acid sensitive drugs may occur (Rawlins, E. A., editor, *Bentley's Textbook of Pharmaceutics*, London: Bailliere, Tindall and Cox, (1977), 291).

Method of Manufacture:

Cellulose acetate phthalate is produced by reacting the partial acetate ester of cellulose with phthalic anhydride in the presence of a tertiary organic base, such as pyridine.

Safety:

Cellulose acetate phthalate is widely used in oral pharmaceutical products and is generally regarded as a nontoxic material, free of adverse effects.

Results of long-term feeding studies with cellulose acetate phthalate, in rats and dogs, have indicated a low oral toxicity. Rats survived daily feedings of up to 300 in the diet for up to one year without showing a depression in growth. Dogs fed 16 g daily in the diet for one year also remained normal (Hodge, H. C., "The Chronic Toxicity of Cellulose Acetate Phthalate in Rats and Dogs", *J. Pharmacol.*, 80, 250–255, (1944)).

Regulatory Status:

Included in the FDA Inactive Ingredients Guide (oral capsules and tablets). Included in nonparenteral medicines licensed in the United Kingdom.

Pharmacopeias: Aust, Br, Braz, Cz, Eur, Fr, Ger, Gr, Hung, Ind, It, Jpn, Mex, Neth, Nord, Port, Swiss and USPNF.

Some of the properties of HPMCP, described in the *Handbook of Pharmaceutical Excipients* are summarized as follows:

Non proprietary Names: BP: Hypromellose phthalate; PhEur: Methylhydroxypropylcellulosi phthalas and USPNF: Hydroxypropyl methylcellulose phthalate.

Synonyms: Cellulose phthalate hydroxypropyl methyl ether; HPMCP; 2-hydroxypropyl methylcellulose phthalate; methylhydroxypropylcellulose phthalate.

Chemical Name and CAS Registry Number: Cellulose, hydrogen 1,2-benzenedicarboxylate, 2-hydroxypropyl methyl ether [9050-31-1].

Structural Formula:

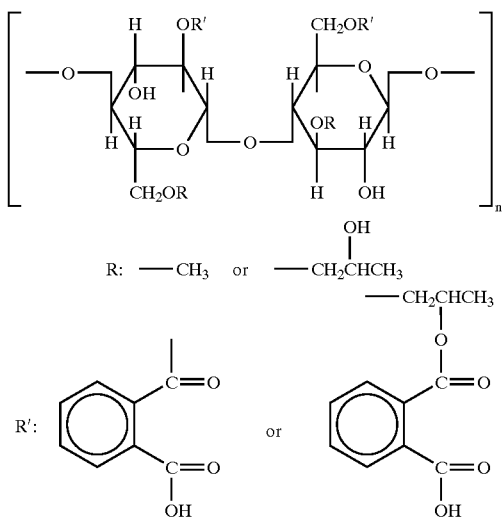

Functional Category: Coating agent.

Applications in Pharmaceutical Formulations or Technology

Hydroxypropyl methylcellulose phthalate has heretofore been widely used in oral pharmaceutical formulations as an enteric coating material for tablets or granules (Ehrhardt, L., Patt, L., Schindler, E., "Optimization of Film Coating Systems", *Pharm. Ind.*, (1973), 35:719–722; Delporte, J. P., Jaminet, F., "Influence of Formulation of Fnteric-Coated Tablets on the Bioavailability of the Drug", *J. Pharm. Belg.*, (1976), 31, 263–276; Patt, L., Hartmann, V., "Solvent Residues in Film Forming Agents", *Pharm. Ind.*, (1976), 38:902–906; Stafford, J. W., "Enteric Film Coating Using Completely Aqueous Dissolved Hydroxypropyl Methylcellulose Phthalate Spray Solutions", *Drug. Dev. Ind. Pharm.*, (1982), 8:513–530; Thoma, K., Heckenmuller, H., Oschmann, R., "Resistance and Disintegration Behaviour of Gastric Juice Resistant Drugs", *Pharmazie*, (1987), 42:832–836; Thoma, K., Heckenmüller, H., Oschmann, R., "Impact of Film Formers and Plasticizers on Stability of Resistance and Disintegration Behaviour", *Pharmazie*, (1987), 42:837–341).

Hydroxypropyl methylcellulose phthalate is insoluble in gastric fluid, but will swell and dissolve rapidly in the upper intestine. Generally, concentrations of 5–10% of hydroxypropyl methylcellulose phthalate were employed with the material being dissolved in either a dichloromethane: ethanol (50:50) or an ethanol: water (80:20) solvent mixture. Hydroxypropyl methylcellulose phthalate can normally be applied to tablets and granules without the addition of a plasticizer or other film formers using established coating techniques (Rowe, R. C., "Molecular Weight Studies on the Hydroxypropyl Methylcellulose Phthalate '(HP55)'", *Acta. Pharm. Technol.*, (1982), 28(2):127–130. However, the addition of a small amount of plasticizer or water can avoid film cracking problems; many commonly used plasticizers such as diacetin, triacetin, diethyl and dibutyl phthalate, castor oil, acetyl monoglyceride and polyethylene glycols are compatible with hydroxypropyl methylcellulose phthalate. Tablets coated with hydroxypropyl methylcellulose phthalate disintegrate more rapidly than tablets coated with cellulose acetate phthalate.

Hydroxypropyl methylcellulose phthalate can be applied to tablet surfaces using a dispersion of the micronized hydroxypropyl methylcellulose phthalate powder in an aqueous dispersion of a suitable plasticizer such as triacetin, triethyl citrate or diethyl tartrate along with a wetting agent (Muhammad, N. A., Boisvert, W., Harris, M. R., Weiss, J., "Evaluation of Hydroxypropyl Methylcellulose Phthalate 50 as Film Forming Polymer from Aqueous Dispersion Systems", *Drug Dev. Ind. Pharm.*, (1992), 18:1787–1797).

Hydroxypropyl methylcellulose phthalate may be used alone or in combination with other soluble or insoluble binders in the preparation of granules with sustained drug release properties; the release rate is pH dependent. Since hydroxypropyl methylcellulose phthalate is tasteless and insoluble in saliva, it can be used as a coating to mask the unpleasant taste of some tablet formulations.

Description:

Hydroxypropyl methylcellulose phthalate occurs as white to slightly off-white colored free-flowing flakes or as a granular powder. It is odorless or with a slightly acidic odor, and a barely detectable taste.

Typical Properties:

Melting Point: 150° C.

Solubility: practically insoluble in ethanol and water; very slightly soluble in acetone, and toluene; soluble in aqueous alkalis, a mixture of equal volumes of acetone and methanol, and in a mixture of equal volumes of dichloromethane and methanol.

Stability and Storage Conditions:

Hydroxypropyl methylcellulose phthalate is chemically and physically stable at ambient temperature and humidity for 3–4 years, and for 2 to 3 months at 40° C. and 75% relative humidity (Shin-Etsu Chemicals Co., Ltd., Technical Literature: Hydroxypropyl Methylcellulose Phthalate, (1993).

Hydroxypropyl methylcellulose phthalate is stable on exposure to UV light for up to 3 months at 25° C. and 70% relative humidity (Shin-Etsu Chemical Co., Ltd., Technical Literature Hydroxypropyl Methylcellulose Phthalate, (1993). In general, hydroxypropyl methylcellulose phthalate is more stable than cellulose acetate phthalate. At ambient storage conditions, hydroxypropyl methylcellulose phthalate is not susceptible to microbial attack.

Incompatibilities:

Incompatible with strong oxidizing agents. Splitting of film coatings has been reported rarely, most notably with coated tablets which contain microcrystalline cellulose and calcium carboxymethylcellulose. Film splitting has also occurred when a mixture of acetone: propan-2-ol or dichloromethane: propan-2-ol has been used as a coating solvent, or when coatings have been applied in conditions of low temperature and humidity. However, film splitting may be avoided by careful selection of the coating solvent used, by using a higher molecular weight grade of polymer (Rowe, RC, "Molecular Weight Studies on the Hydroxypropyl Methylcellulose Phthalate '(HP55)'", *Acta. Pharm. Technol.*, (1982), 28(2):127–130), or by the addition of a plasticizer, such as acetyl monoglyceride or triacetin. The addition of more than about 10% titanium dioxide to a coating solution of hydroxypropyl methylcellulose phthalate, that is used to produce a colored film coating, may result in coatings with decreased elasticity and gastric fluid resistance (Shin-Etsu Chemical Co., Ltd., Technical Literature: Hydroxypropyl Methylcellulose Phthalate, (1993)).

Method of Manufacture:

Hydroxypropyl methylcellulose acetate phthalate is prepared by the esterification of hydroxypropyl methylcellulose with phthalic anhydride. The degree of methoxy and phthalyl substitution determines the properties of the polymer and in particular the pH at which it dissolves in aqueous media.

Safety:

Hydroxypropyl methylcellulose phthalate has been heretofore used widely, primarily as an enteric coating agent, in oral pharmaceutical formulations. Chronic and acute animal feeding studies on several different species have shown no evidence or teratogenicity or toxicity associated with hydroxypropyl methylcellulose phthalate (Kitagawa, H., Kawana, H., Satoh, T., Fukuda, Y., "Acute and Subacute Toxicities of Hydroxypropyl Methylcellulose Phthalate", *Pharmacometrics*, (1970), 4(6):1017–1025; Kitagawa, H., Satoh, T., Yokoshima, T., Nanbo, T., "Absorption, Distribution and Excretion of Hydroxypropyl Methylcellulose Phthalate in the Rat", *Pharmacometrics*, (1971), 5(1):1–4; Ito, R., Toida, S., "Studies on the Teratogenicity of a New Enteric Coating Material, Hydroxypropyl Methylcellulose Phthalate (HPMCP) in Rats and Mice", *J. Med. Soc. Toho-Univ.*, (1972), 19(5):453–461; Kitagawa, H., Yano, H., Fukuda, Y., "Chronic Toxicity of Hydroxypropylmethylcellulose Phthalate in Rats", *Pharmacometrics*, (1973), 7(5);689–701; Kitagawa, H., Yokoshima, T., Nanbo, T., Hasegawa, M., "Absorption, Distribution, Excretion and Metabolism of $^{14}$C-hydroxypropyl Methylcellulose Phthalate", *Pharmacometrics*, (1974), 8(8):1123–1132. Hydroxypropyl methylcellulose phthalate is generally regarded as a nonirritant and nontoxic material. $LD_{50}$ (rat, oral): >15 g/kg (Kitagawa et al., *Pharmacometrics*, (1970), 4(6):1017–1025).

Regulatory Status: included in the FDA Inactive Ingredients Guide (oral capsules and tablets) and included in nonparenteral medicines licensed in the United Kingdom.

Pharmacopeias; Br, Eur, Fr, Gr, It, Jpn, Neth, Port, Swiss and USPNF.

A particularly preferred composition for vaginally administering to a human in accordance with the present invention comprises a micronized preparation containing CAP or micronized HPMCP, a poloxamer and distilled acetylated monoglycerides (a mixture of micronized CAP, poloxamer and acetylated monoglycerides is sold by the FMC Corporation under the trade name "AQUATERIC") suspended in glycerol. A poloxamer is a nonionic polyoxyethylene-polyoxypropylene copolymer. Squalane (2,6,10,15,19,23-hexamethyltetracosane) can be used instead of glycerol.

A chemical name for a poloxamer is α-hydro-ω-hydroxypoly-(oxyethylene) poly(oxypropylene) poly(oxyethylene) block copolymer. The poloxamer polyols are a series of closely related block copolymers of ethylene oxide and propylene oxide conforming to the following formula:

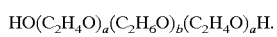

The following is a list of grades of poloxamers (USPNF XVII):

| Poloxamer | Physical Form | a | b | Average Molecular Weight |
|---|---|---|---|---|
| 124 | Liquid | 12 | 20 | 2,090 to 2,360 |
| 188 | Solid | 80 | 27 | 7,680 to 9,510 |
| 237 | Solid | 64 | 37 | 6,840 to 8,830 |
| 338 | Solid | 141 | 44 | 12,700 to 17,400 |
| 407 | Solid | 101 | 56 | 9,840 to 14,600 |

To prevent separation from the glycerol of the microsuspension containing CAP or HPMCP, the poloxamer and the distilled acetylated monoglycerides, it is preferred to add polyvinlpyrrolidone ("PVP") and a 1-ethenyl-2-pyrrolidinone homopolymer (Crospovidone) (Polyplasdone) $(C_6H_9NO)_n$, molecular weight >1,000,000) (water insoluble synthetic cross-linked homopolymer of N-vinyl-2-pyrrolidinone).

The term micronized used herein refers to particles having a particle size of less than 35 microns, preferably less than 15 microns, more preferably less than 10 microns and most preferably less than 5 microns.

In the composition described herein which includes glycerol, the glycerol may be replaced with a saline solution or water, so long as the composition is stored at <25° C.

CAP is commonly used as an enteric film coating material or as a matrix binder for tablets and capsules. Its safety has been extensively studied and it has been shown to be free of adverse effects. Vaginal irritation tests in the rabbit model further confirmed its safety. CAP is a high molecular weight compound ($M_w$ is approximately 60,000), indicating that if topically applied, it will not spread systemically. The likelihood of CAP spreading beyond the site of application has been further decreased by using it in a micronized form.

A preferred composition for administration in the present invention can be made as follows: dissolve PVP in glycerol, then add cross-linked I-ethenyl-2-pyrrolidinone homopolymer (Crospovidone) (Crospovidone is cross-linked povidone) and a composition comprising micronized CAP and poloxamer and acetylated monoglycerides. The PVP and cross-linked 1-ethenyl-2-pyrrolidinone homopolymer would be in concentrations sufficient to stabilize the suspension of "AQUATERIC" in glycerol. Squalane can be used instead of glycerol.

In the methods of the present invention, a pharmaceutically effective anti-bacterial vaginosis amount, respectively, of CAP or HPMPC or both CAP and HPMPC is administered to a human female. The composition for use in the present invention is administered to the vagina.

The method of the present invention can be carried out by vaginal administration, such as by administering a cream, ointment, lotion, jelly, solution, emulsion or foam formulation containing a pharmaceutically effective anti-bacterial vaginosis amount of CAP (such as micronized CAP) or HPMCP (such as micronized HPMCP) or both, either alone or in combination with a pharmaceutically acceptable carrier or diluent.

Alternatively, CAP or HPMCP or both can be applied on a pessary or tampon for vaginal administration. The pharmaceutical formulation for topical administration would comprise a pharmaceutically effective anti-bacterial vaginosis amount of CAP or HPMCP or both CAP and HPMCP and at least one pharmaceutically acceptable topical carrier or diluent, to form an ointment, cream, gel, lotion, paste, jelly, spray or foam.

The amount (dosage) of the active ingredient (CAP or HPMCP or both CAP and HPMCP) in a topical formulation for use in the present invention will, in general, be less than 1,000 milligrams, preferably between 200 to 800 milligrams.

It is preferable to administer the active ingredient (CAP, HPMCP or both CAP and HPMCP) in conjunction with a pharmaceutically acceptable diluent or carrier, as a pharmaceutical formulation. The present invention thus also involves the use of a pharmaceutical formulation or composition comprising the active ingredient together with one or more pharmaceutically acceptable carriers or diluents and, optionally, other prophylactic ingredients. The carrier (s) or diluent(s) should be "acceptable" in the sense of being compatible with the other ingredients of the formulation and not deleterious to the recipient.

Pharmaceutical formulations include those suitable for vaginal or topical administration. The formulations may, where appropriate, be conveniently presented in discrete dosage units and may be prepared by any of the methods well known in the art of pharmacy. All such methods include the step of bringing into association the active ingredient with liquid carriers, gels or finely divided solid carriers or both and then, if necessary, shaping the product into the desired formulation.

Formulations suitable for vaginal administration may be presented as pessaries, tampons, creams, gels, pastes, jelly, foams or sprays or aqueous or oily suspensions, solutions or emulsions (liquid formulations) containing in addition to the active ingredient, such carriers as are known in the art to be appropriate.

Pharmaceutical formulations and preparations suitable for administration may conveniently be presented as a solution, an aqueous or oily suspension, or an emulsion. The active ingredient may also be presented as a bolus, electuary or paste.

Liquid preparations for vaginal administration may contain conventional additives such as suspending agents, emulsifying agents, non-aqueous vehicles (which may include edible oils) or preservatives.

Pharmaceutical formulations suitable for vaginal administration, wherein the carrier is a solid, are most preferably represented as unit dose suppositories. Suitable carriers include cocoa butter and other materials commonly used in the art, and the suppositories may be conveniently formed by admixture of the active compound with the softened or melted carrier or carriers followed by chilling and shaping in molds.

Drops may be formulated with an aqueous or non-aqueous base comprising one or more dispersing agents, solubilizing agents or suspending agents. Liquid sprays are conveniently delivered from pressurized packs.

When desired, the above described formulations adapted to give sustained release of the active ingredient may be employed.

Pharmaceutical compositions for use in the present invention can contain 1 to 25 wt. %, preferably 5 to 20 wt. % and, more preferably, 12 to 18 wt. % of micronized cellulose acetate phthalate and glycerol and either polyvinylpyrrolidone and crospovidone (1-ethenyl-2-pyrrolidinone homopolymer), or colloidal silicon dioxide, to form an easily applicable homogeneous cream.

In addition to the formulations disclosed above, a semi-solid formulation containing all solid ingredients (i.e., "AQUATERIC", povidone, crospovidone and colloidal silicone dioxide) can be mixed with glycerol or squalane wherein the amounts of all the components are sufficient to result in a semi-solid dough or putty which can be easily shaped, aliquotted into desired portions and packaged for protection from environmental factors (humidity, etc.).

Moreover, the "AQUATERIC" can be replaced by another form of micronized CAP. This could be obtained, for example, by dissolving 100 mg of CAP and 100 mg of polyvinylpyrrolidone (povidone, PVP) per 1 ml of dimethyl sulfoxide. After dissolution of the solid components, water is slowly added under efficient, vigorous mixing. This will result in the formation of a fine precipitate of CAP containing PVP. The precipitate is subsequently washed with water and finally freeze-dried. The fine, freeze-dried powder can be used instead of the "AQUATERIC".

The procedure disclosed in the preceding paragraph is much simpler than a similar procedure utilizing polyvinyl alcohol instead of PVP, and acetone instead of dimethyl sulfoxide, and also requires the presence of a mineral salt, such as magnesium chloride (USP 4,968,350 to Bindschaedler et al., "Process for Preparing a Powder of Water-insoluble Polymer which can be Redispersed in a Liquid Phase, the Resulting Powder and Utilization Thereof"). The presence of $Mg^{++}$ is also undesirable, since it decreases the stability of CAP.

The aforementioned formulation of "AQUATERIC", PVP and Crospovidone or of "AQUATERIC" and colloidal silicon dioxide in glycerol is suitable for topical application. However, in order to apply (administer) the formulation in predetermined quantities, in addition to the formulation, a measuring device, e.g., an applicator, should be provided.

It will be advantageous to incorporate the formulations containing CAP and/or HPMCP into hydroxypropyl methylcellulose capsules such as "VEGI CAPS" or "VEGGIE-CAPS", manufactured by GS Technologies, Springville, Utah, USA, which can be configured as vaginal suppositories. This would reduce costs and avoid possible disposal problems. Such suppositories can be inserted into the vagina intact, whereby the shell of the capsule will soften and rupture upon interaction with moisture within the vagina, thus releasing the CAP and/or HPMCP formulation.

For example, the above-described hydroxypropyl methylcellulose capsules can be filled with "AQUATERIC" suspended in glycerol.

The formulation containing the active ingredient (CAP and/or HPMCP) of the present invention can be in the form of a single capsule or the formulation may be in the form of two or more capsules, each containing the same or distinct ingredients.

EXAMPLES

Summary

Suspensions of *Gardnerella vaginalis, Mycoplasma hominis, Mycoplasma capricolum, Mobiluncus curtisii,* and *Prevotella corporis* were mixed with an equal volume of micronized CAP formulated into a cream, and incubated at 37° C. for 15 and/or 5 minutes. Subsequently, the mixtures were serially diluted 10-fold, and each dilution was plated onto agar plates. After incubation at 37° C. under appropriate conditions for each organism, the bacterial colonies were counted.

Results: Exposure of the five selected microorganisms associated with bacterial vaginosis to the CAP containing cream resulted in a $\geq 10^5$-fold decrease in viability.

Conclusions: Earlier results indicated that an appropriately formulated CAP containing cream acts as a broad spectrum microbicide that has potential to prevent the transmission of viral and bacterial STD pathogens. The results presented hereinbelow indicate that the CAP containing cream is also a therapeutic or prophylatic agent for bacterial vaginosis and, thus, further contributes to protection against acquisition of STDs, including HIV-1 infection.

Materials and Methods

Cap Formulations

The preparation of micronized CAP, namely "AQUATERIC" containing 66–73 weight% CAP, a polyoxyethylene-polyoxypropylene block copolymer and distilled acetylated monoglycerides, used in aqueous media as an enteric film coating liquid (FMC Corporation, Philadelphia, Pa., USA) (15.9 g) was mixed with glycerol (70.2 g). In Formulation I ("NYB92A"), polyvinylpyrrolidone K-30 (Spectrum Quality Products Inc., New Brunswick, N.J., USA) (11.1 g) and crospovidone NF (ISP Technologies, Inc., Wayne, N.J., USA) (2.8 g) were added to maintain the micronized CAP in suspension. In Formulation II ("NYB122A"), polyvinylpyrrolidone+crospovidone were replaced with 7.89 g of colloidal silicone dioxide M-5P (Cabot Corp., Cab-C-Sil Division, Tuscola, Ill., USA), an excipient with an established use in vaginal preparations, *Handbook of Pharmaceutical Excipients*, Wade, A. and Weller, P. J., eds., American Pharmaceutical Association, 2nd Ed., (1994)) per 23.7g of "AQUATERIC"+100 g glycerol. Control creams lacking CAP (designated as Formulation I ("NYB92A" ⊖ CAP) and Formulation II ("NYBC122A" ⊖ CAP) were also prepared.

Preparation of Bacterial Stocks

All bacteria were obtained from the American Type Culture Collection (ATCC). *Gardnerella vaginalis* (ATCC #14018) was grown in ATCC #1685 broth under conditions provided by the ATCC and on V blood agar plates (Dunkelberg, Jr., W. E., McVeigh, I., "Growth Requirements of *Haemophilus vaginalis*", *Antonie van Leeuwenhoek*, 35, 129–145, (1969); Totten, P. A., Amsel, R., Hale, J., Piot, P., Holmes, K. K., "Selective Differential Human Blood Bilayer Media for Isolation of Gardnerella (Haemophilus) Vaginalis", *J. Clin. Microbiol.*, 15, 141–147, (1982)) (Fisher Scientific, Pittsburgh, Pa., USA; Cat. #4321874). *Mycoplasma hominis* (ATCC #14027) and *Mycoplasma capricolum* (ATCC #23205) were grown in ATCC liquid media #243 and #247, respectively, and or colony counting, the corresponding agar plates (Agar Noble; Difeo 0142) were used. The liquid cultures were maintained under aerobic conditions at 37° C. and the agar plates were incubated in the presence of $CO_2$ (5% at 37° C.).

*Prevotella corporis* (ATCC #33547) and *Mobiluncus curtisii* (ATCC #35241) were grown in ATCC media 1490 and 1015, respectively. Blood agar plates were used for growth and colony counting. One set of plates for each organism was incubated at 37° C. in an anaerobic jar containing a commercial gas pack generating an atmosphere of 50. $CO_2$, 10% $H_2$, 85% $N_2$ while the other set of plates was used in the presence of $O_2$ to certify the absence of aerobic microorganisms in the cultures.

Isolated colonies were used to check for the typical characteristics of *Prevotella corporis* and *Mobiluncus curtisii*. These are: 1) Visual observation: *Prevotella corporis* should produce after 5 days of culture white colonies becoming black after 2 weeks. *Mobiluncus curtisii* should produce after 3 days of culture tiny translucent smooth and convex colonies; 2) Gram staining; 3) Catalase test; 4) Absence of growth in the presence of $O_2$.

One colony from the ascertained pure culture was then plated on new blood plates once weekly.

Assessment of the Bactericidal Activity of CAP Formulations Equal volumes of the Formulation II and suspensions of the respective bacteria (Gardnerella and Mycoplasmas; $1 \times 10^8$ to $1 \times 10^9$ cells/ml in 0.14 M NaCl) were mixed and incubated at 37° C. for 15 minutes. The effects of the Formulations I and the control formulations (Formulation I ⊖ CAP and Formulation II β CAP) on *Gardnerella vaginalis* were determined under similar conditions. Mixtures of the formulations with the bacteria were subsequently neutralized by adding 50 μl of 0.43 M $Na_3PO_4 \cdot 12 H_2O/1$ ml of the suspension. After 5 minutes at 20° C. and intermittent mixing, the neutralized suspensions were serially diluted 10-fold in the appropriate broth media. A 20 μl aliquot of each dilution was inoculated onto agar plates and incubated for 72 hours at 37° C. under aerobic conditions with 5% $CO_2$. Subsequently the number of colonies corresponding to each dilution was counted. Control experiments using phosphate buffered saline ("PBS") instead of the formulations were included with each experiment. For Mycoplasmas, in addition, 5 ml of each dilution was incubated under similar conditions using a shaker and the turbidity of the suspensions was determined after completed incubation.

The bactericidal activity of Formulation II against *Prevotella corporis* and *Mobiluncus curtisii* was determined under the following conditions. A 0.3 g aliquot of Z. Formulation II was placed into a sterile 2 ml vial, capped with a cotton plug and incubated overnight in a glove box under a flask of an anaerobic gas mixture ("AGM": 80% $N_2$ 10% $H_2$ and 10% $CO_2$). The vials were capped and sealed before removing them from the glove box. In a laminar flow hood, 0.3 ml aliquots of the bacterial suspensions (inoculum) were added to the 0.3 g of the cream, vortexed and incubated or 5 or 15 minutes a 37° C. after the cream mixture became homogeneous. Subsequently, the mixtures were neutralized by addition of 0.52 ml of 0.1 M $Na_3PO_4$ which had been made anaerobic and was heat-sterilized and incubated for 5 minutes at 37° C. Serial 10-fold dilutions were made from the mixtures and 100 μl aliquots of the different dilutions (undilute to $10^{-6}$) were plated in duplicate on agar plates and incubated at 37° C. in anaerobic jars for 5 days for *Prevotella corporis* and 3 days for *Mobiluncus curtisii*. The colonies were counted and the results were expressed as the mean colony forming units (CFU)±standard error of the mean ("SEM").

The dilution medium for *Prevotella corporis* and *Mobiluncus curtisii* (1.5 g/100 ml of peptone water, 0.17 g/100 ml [10 mM] $K_2HPO_4$, brought to a pH of 7.0 with 1N HCl, 0.4 ml/100 ml of 0.025% Resazurin) was boiled under reflux for 15 minutes and cooled under a flux of an anaerobic gas mixture in a vial (10 ml/vial), capped and sealed with aluminum and heat-sterilized. Prior to use, the medium was reduced with a solution of cysteine (0.2 ml/10 ml of a solution of 25 mg cysteine/ml), obtained by adding water boiled for 15 minutes to a cysteine-containing flask sparked with an anaerobic gas mixture. The solution was cooled, capped and autoclaved.

One ml of the reduced dilution medium was added to a one or two week old culture of the respective microorganism on the blood plates. The bacteria were suspended by stirring the surface of the plates with a sterile glass hockey stick and transferred back to a vial containing the remaining 9 ml of the dilution medium. The $OD_{600}$ of this suspension was read and the volume adjusted to a final $OD_{600}$ of 0.1. Then 0.1 ml of the resulting suspension was spread over an anaerobic blood plate. After 5 days, the microorganisms growing on this plate were suspended as described above and diluted to an $OD_{600}$ of 0.1. The latter suspension was used as the inoculum. Positive control cultures corresponded to serially diluted inoculum, 0.1 ml aliquots of which were plated in duplicate onto blood agar plates and incubated as described above.

Figure 1B:
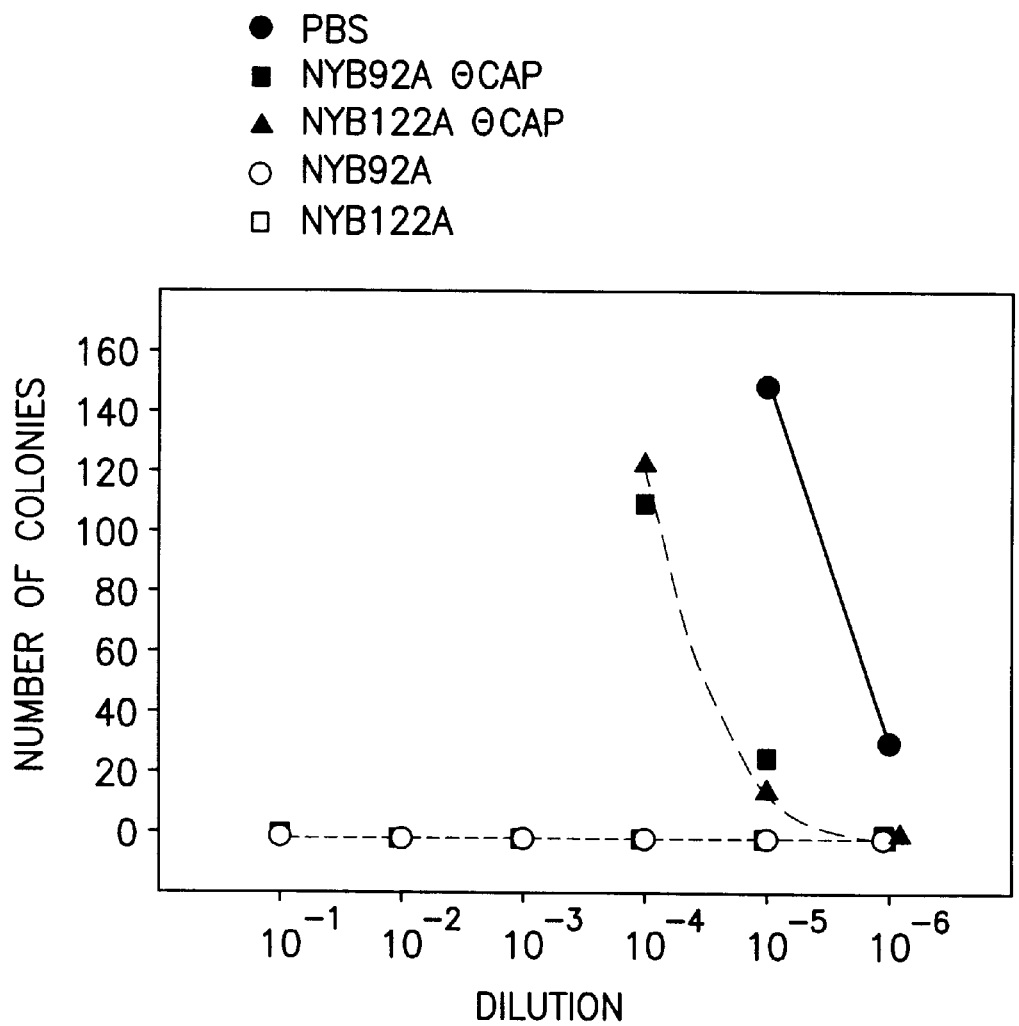

To consider the possibility that small amounts of $O_2$ which may have remained trapped in the cream, could limit the bacterial growth, a control corresponding to "aerobic PBS" was included in the experiments. A 0.3 ml aliquot of the inoculum was added to 0.3 ml of heat-sterilized PBS that had not been treated to remove oxygen. The mixture was vortexed and incubated for 15 minutes at 37° C. and then serially diluted 10-fold. Subsequently, 0.1 ml of the dilutions were plated in duplicate on blood agar plates and incubated as described above. Results The replicative capacity of *Gardnerella vaginalis* exposed to the Formulations I or II of CAP was dramatically decreased (>$10^5$-fold), as compared with bacteria exposed to PBS (FIG. 1). By comparison, the control formulations lacking CAP had a much lesser effect on bacterial viability. Results of in vivo experiments in the mouse model for vaginal HSV-2 infection indicated that the Formulation II was much more effective in preventing infection than Formulation I. For this reason, the Formulation II was selected for further experiments to evaluate its bactericidal activity against organisms associated with bacterial vaginosis. The exposure of Mycoplasma hominis and Mycoplasma capricolum to Formulation II for 15 minutes at 37° C. resulted in a significant reduction of the number of CFUs (>$10^5$-fold; data not shown).

The *Prevotella corporis* and *Mobiluncus curtisii* strains of bacteroides, suspended in the respective liquid media suggested by the ATCC, were plated either onto blood agar plates or onto anaerobic Columbia pre-reduced blood agar plates, and incubated at 37° C. in anaerobic jars in an anaerobic gas mixture atmosphere. Both bacteroide strains grew well on both types of plates and proved to be pure cultures as confirmed by: a) colony morphology; b) absence of catalase and oxidase in both species; and c) Gram stain negativity.

Figure 2A:
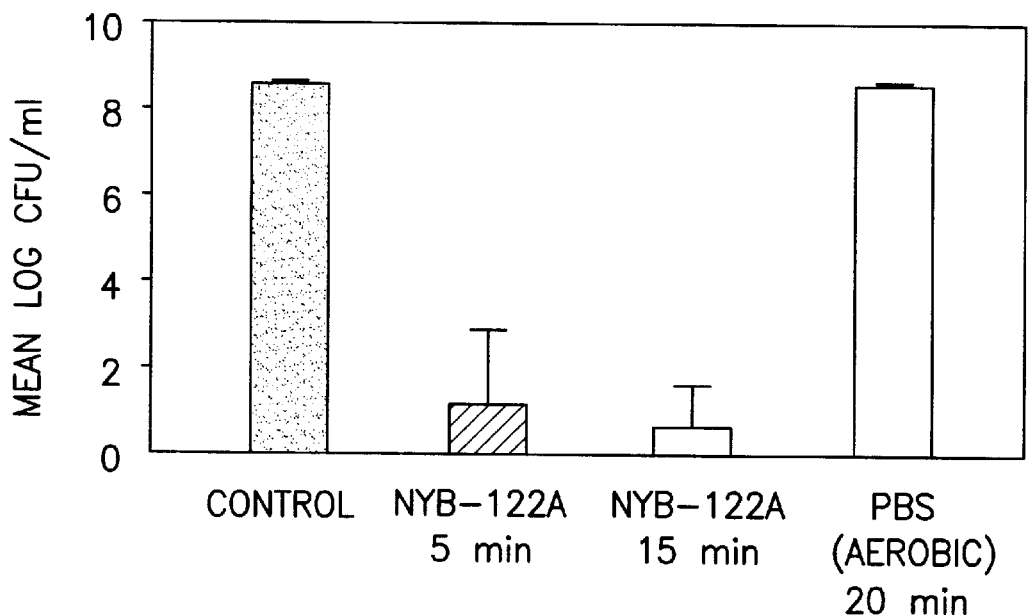
FIGS. 2A and 2B are graphs showing the survival of *Prevotella corporis* (FIG. 2A) and *Mobiluncus curtisii* (FIG. 2B) in the presence of the CAP containing Formulation II described hereinbelow. Results of duplicate experiments repeated three times are presented. The last columns on the right correspond to results obtained with bacteria exposed to phosphate buffered saline ("PBS") from which oxygen has not been removed.
Figure 2B:
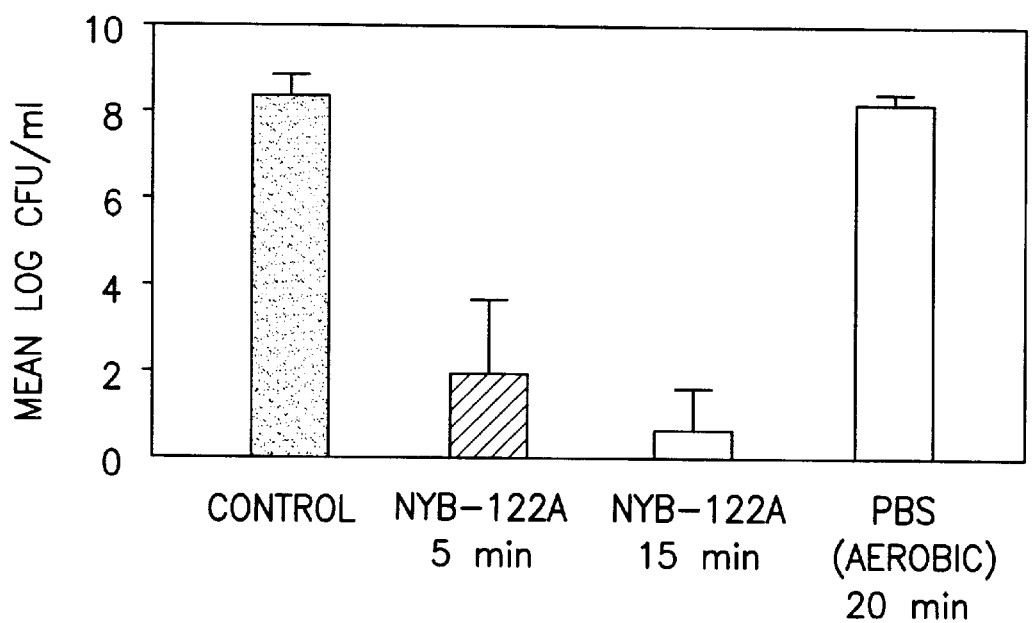

The results shown in FIG. 2 clearly demonstrate that the Formulation II had a bactericidal activity against both bacteroides species after a 5 minute exposure at 37° C. ($\approx 10^6$-fold reduction of CFUs). This effect cannot be attributed to the possible presence of remaining oxygen in the Formulation II cream, as indicated by results obtained with "aerobic PBS".

The results for the inactivation of organisms associated with BV using the CAP cream of the present invention is summarized in the following Table.

| | cfu/mL | |
|---|---|---|
| Organism | before CAP treatment | after CAP |
| G. vaginalis | $2.4 \times 10^7$ | $<10^1$ |
| M. hominis | $3.7 \times 10^6$ | $<10^1$ |
| M. curtisii | $2.0 \times 10^8$ | $5.0 \times 10^0$ |
| P. corporis | $4.0 \times 10^8$ | $5.0 \times 10^0$ |

The results presented hereinabove indicate that the CAP Formulation II inactivated in vitro five selected aerobic and anaerobic bacterial strains associated with bacterial vaginosis, known to place women at increased risk for other genital infections (Sewankambo, N., Gray R. H., Wawer et al., M. J., "HIV-1 Infection Associated with Abnormal Vaginal Flora Morphology and Bacterial Vaginosis", *Lancet*, 350, 546–550, (1997); Taha, T. E., Hoover, D. R., Dallabeta et al., G. A., "Bacterial Vaginosis and Disturbances of Vaginal Flora: Association with Increased Acquisition of HIV", AIDS, 12, 1699–1706, (1998); Hill, G. B., "The Microbiology of Bacterial Vaginosis", *Am. J. Obstet. Gynecol.*, 169, 450–454, 91993)).

These results indicate that a single wide spectrum microbicidal CAP formulation can be used both prophylactically to prevent the sexual transmission of several STDs, including HIV, and therapeutically to ameliorate bacterial vaginosis, and thereby further decrease the probability of sexual transmission of STDs.

It will be appreciated that the instant specification is set forth by way of illustration and not limitation, and that various modifications and changes may be made without departing from the spirit and scope of the present invention.

What is claimed is:

1. A method for treating or preventing bacterial vaginosis caused by a microorganism selected from the group consisting of *Mycoplasma hominis, Mycoplasma capricolum, Mobiluncus curtisii* and *Prevotella corporis* comprising administering to a human female in need thereof a composition comprising an effective anti-bacterial vaginosis amount of at least one active compound selected from the group consisting of cellulose acetate phthalate and hydroxypropyl methylcellulose phthalate, either alone or in combination with a pharmaceutically acceptable carrier.

2. The method of claim 1, wherein the at least one active compound is cellulose acetate phthalate.

3. The method of claim 1, wherein the at least one active compound is hydroxypropyl methylcellulose phthalate.

4. The method of claim 1, wherein the active compounds comprise cellulose acetate phthalate and hydroxypropyl methylcellulose phthalate.

5. The method of claim 2, wherein the bacterium associated with the bacterial vaginosis is *Mycoplasma hominis*.

6. The method of claim 2, wherein the bacterium associated with the bacterial vaginosis is *Mycoplasma capricolum*.

7. The method of claim 2, wherein the bacterium associated with the bacterial vaginosis is *Mobiluncus curtisii*.

8. The method of claim 2, wherein the bacterium associated with the bacterial vaginosis is *Prevotella corporis*.

9. The method of claim 2, wherein the composition comprises micronized cellulose acetate phthalate and colloidal silicon dioxide.

10. The method of claim 2, wherein the composition comprises micronized cellulose acetate phthalate, a polyoxyethylene-polyoxypropylene block copolymer, distilled acetylated monoglycerides, glycerol and colloidal silicon dioxide.

11. The method of claim 2, wherein the composition is topically administered.

12. The method of claim 9, wherein the composition is in the form of a cream and is topically administered to the vagina.

13. The method of claim 10, wherein the composition is in the form of a cream and is topically administered to the vagina.

14. The method of claim 13, wherein the bacterium associated with the bacterial vaginosis is *Mycoplasma hominis*.

15. The method of claim 13, wherein the bacterium associated with the bacterial vaginosis is *Mycoplasma capricolum*.

16. The method of claim 13, wherein the bacterium associated with the bacterial vaginosis is *Mobiluncus curtisii*.

17. The method of claim 13, wherein the bacterium associated with the bacterial vaginosis is *Prevotelia corporis*.

18. The method of claim 1, wherein the method is for treating bacterial vaginosis.

\* \* \* \* \*